United States Patent [19]
D'Amico

[11] Patent Number: 5,279,579
[45] Date of Patent: Jan. 18, 1994

[54] SELF-RECAPPING INJECTION NEEDLE ASSEMBLY

[76] Inventor: Elio D'Amico, 1358 Ashley La., Addison, Ill. 60101

[21] Appl. No.: 957,425

[22] Filed: Oct. 6, 1992

Related U.S. Application Data

[63] Continuation-in-part of Ser. No. 694,549, May 2, 1991, Pat. No. 5,222,947, which is a continuation-in-part of Ser. No. 510,627, Apr. 18, 1990, abandoned.

[51] Int. Cl.⁵ .............................................. A61M 5/32
[52] U.S. Cl. ................................. 604/192; 604/198
[58] Field of Search ............... 604/198, 110, 187, 192, 604/263

[56] References Cited

U.S. PATENT DOCUMENTS

| | | | |
|---|---|---|---|
| 4,695,274 | 9/1987 | Fox | 604/198 |
| 4,772,272 | 9/1988 | McFarland | 604/198 |
| 4,801,295 | 1/1989 | Spencer | 604/198 |
| 4,816,022 | 3/1989 | Poncy | 604/198 |
| 4,863,435 | 9/1989 | Sturman et al. | 604/263 X |
| 4,923,447 | 5/1990 | Morgan | 604/198 |
| 4,929,232 | 5/1990 | Sweeney | 604/111 |
| 4,929,237 | 5/1990 | Medway | 604/198 |
| 5,106,379 | 4/1992 | Leap | 604/198 |

Primary Examiner—John D. Yasko
Attorney, Agent, or Firm—Hill, Steadman & Simpson

[57] ABSTRACT

A sleeve cover for an injection needle assembly or I.V. catheter assembly is slidably engaged to a hub and urged toward its protective position by a spring. A longitudinal groove in a side wall of the sleeve cover guides a pin protruding radially from the hub between protective and unprotective positions. When the sleeve cover is shifted rearwardly by the spring, the needle is exposed, and the sleeve is held by a locking mechanism projecting from the hub. When the locking mechanism is released, the cover shifts to its protective position. The needle assembly or I.V. catheter assembly may then be safely resealed for disposal.

16 Claims, 7 Drawing Sheets

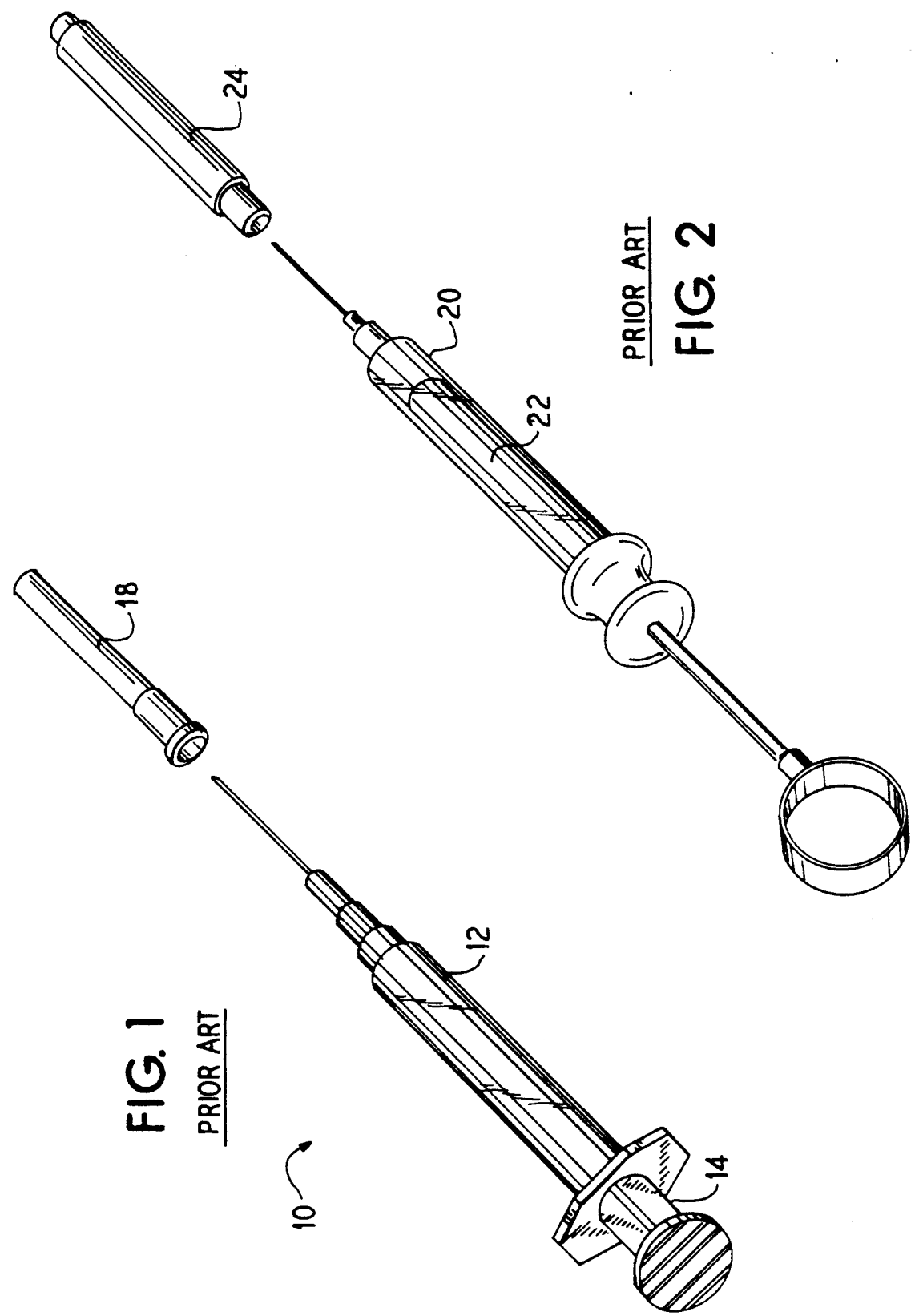

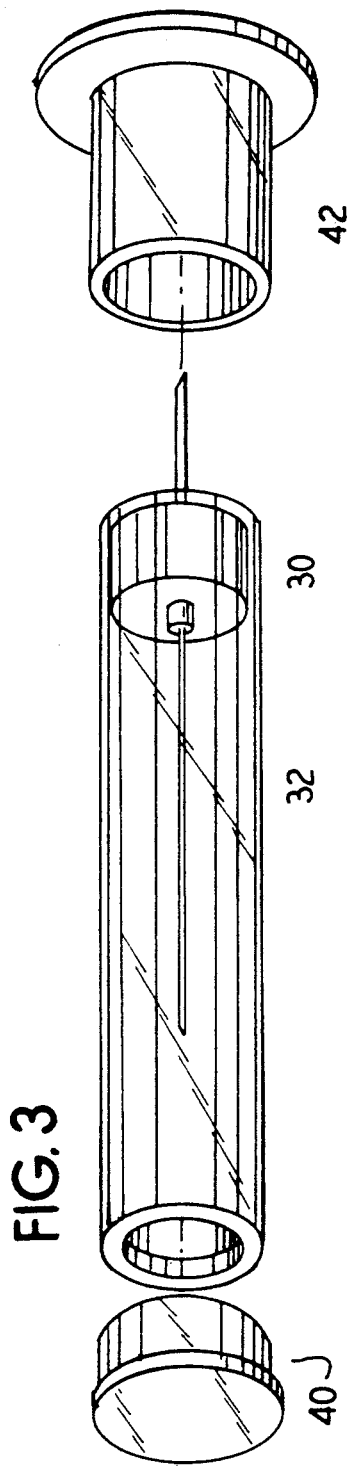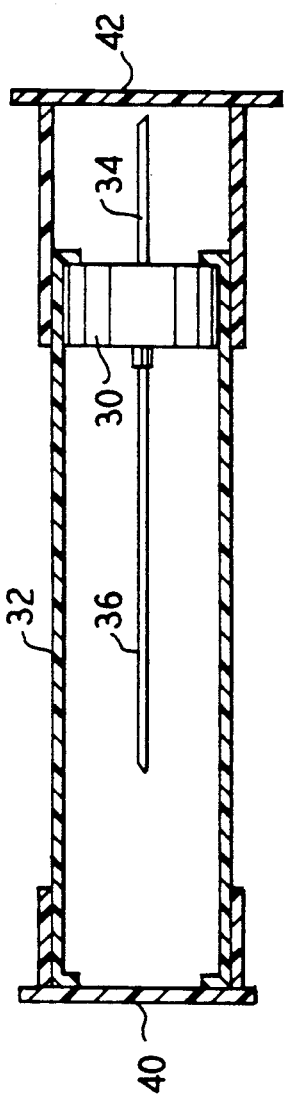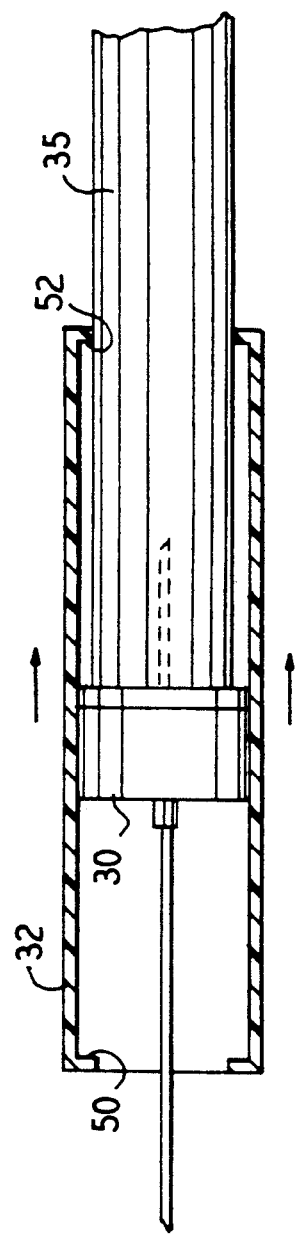

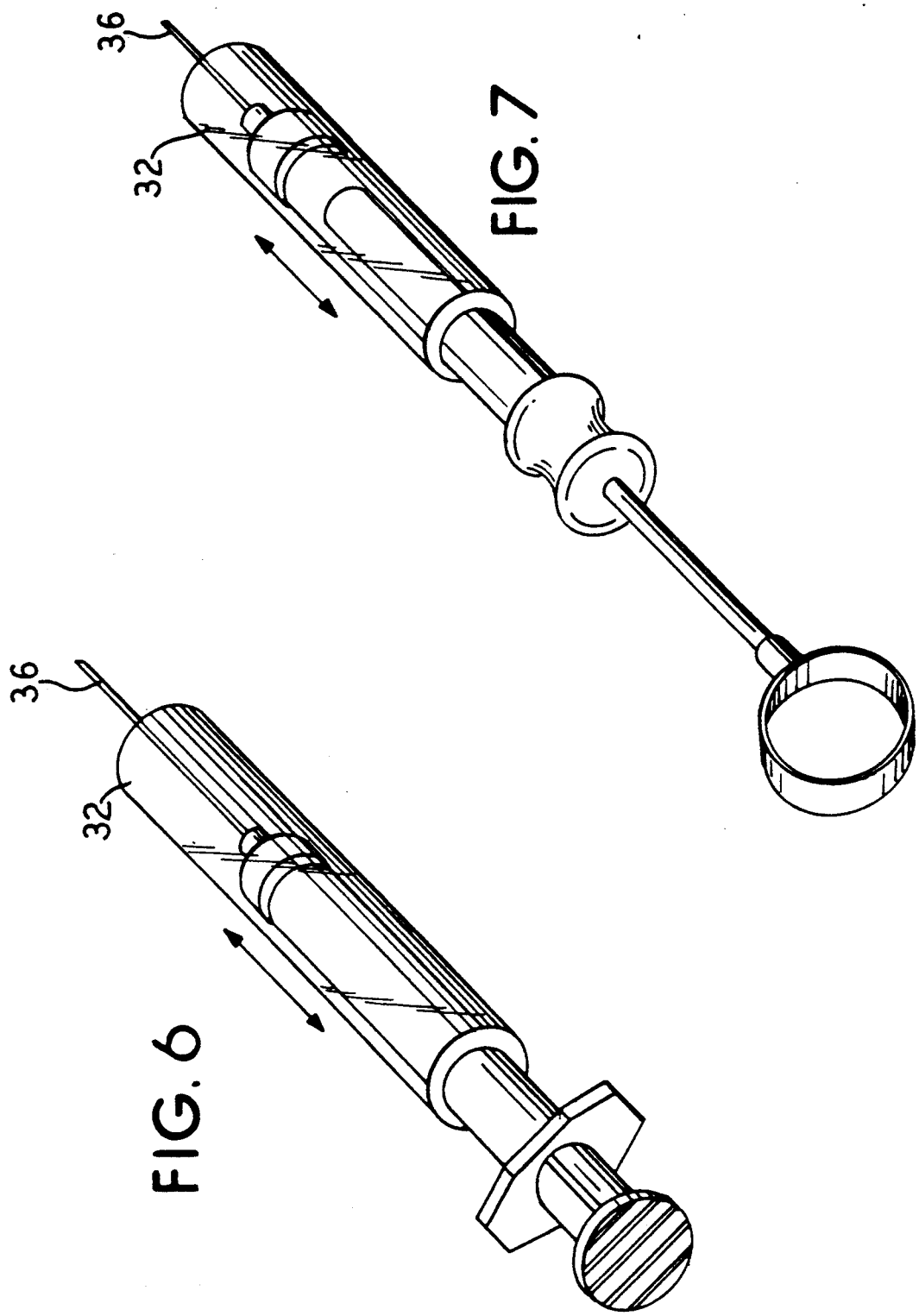

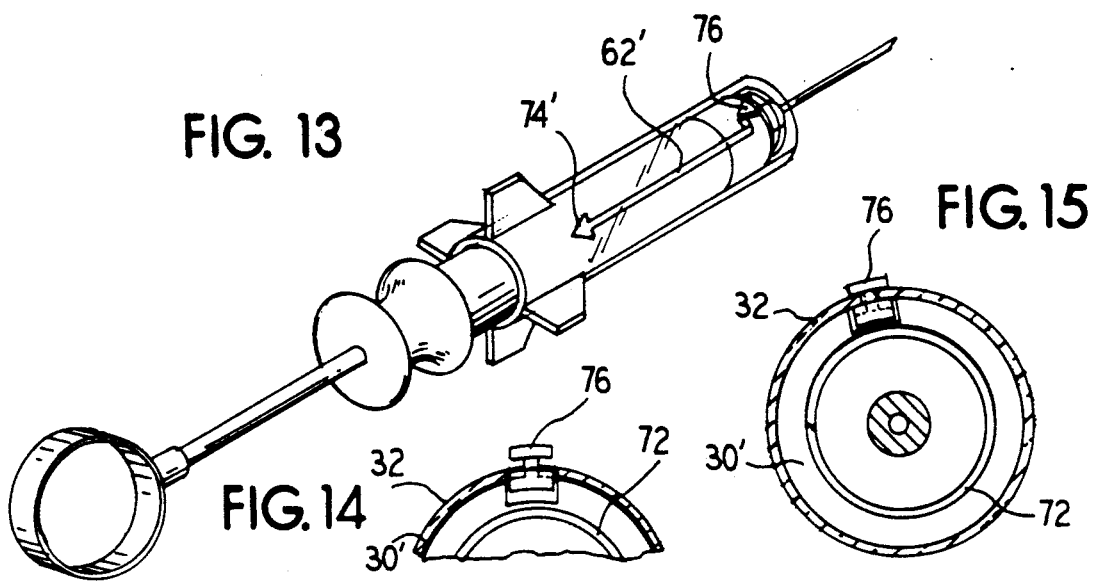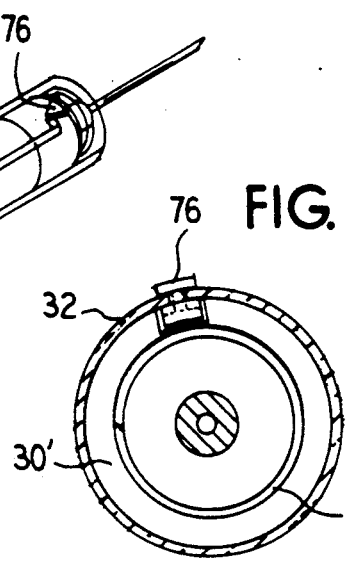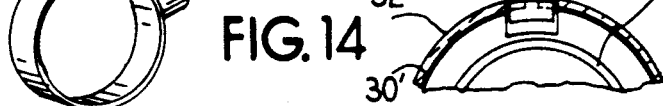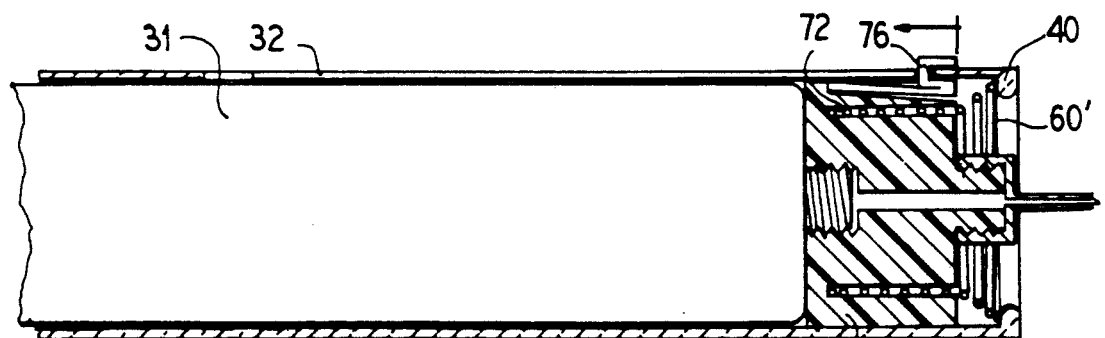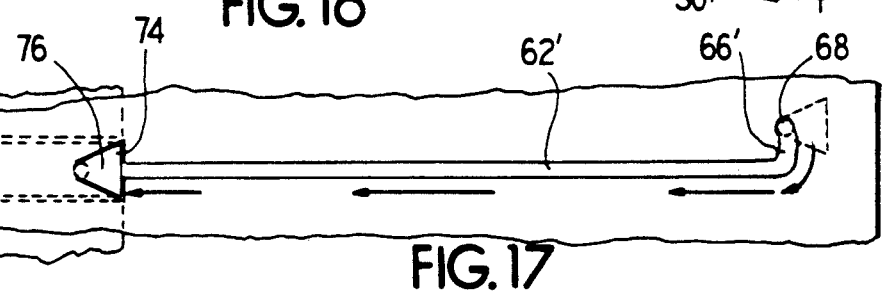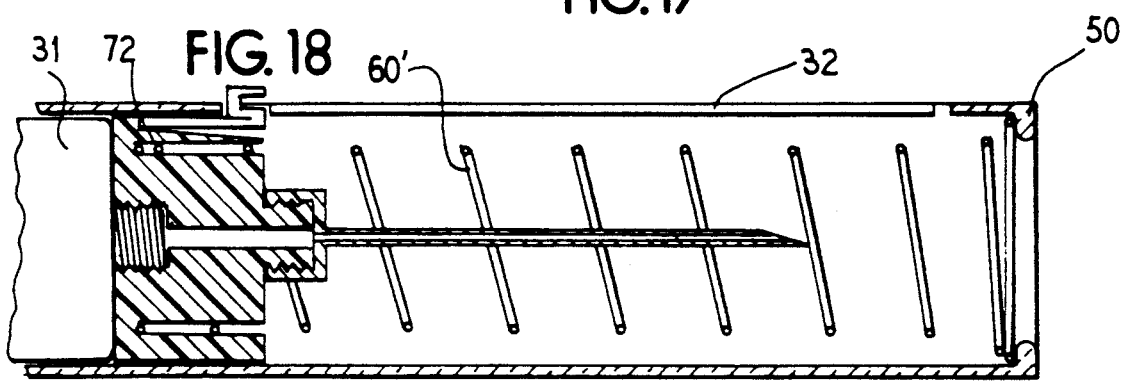

SELF-RECAPPING INJECTION NEEDLE ASSEMBLY

This is a continuation-in-part of U.S. patent application Ser. No. 07/694,549, filed May, 2, 1991 now issued as U.S. Pat. No. 5,222,947 filed Apr. 18, 1990 which is a continuation-in-part of U.S. patent application Ser. No. 07/510,627, now abandoned.

BACKGROUND OF THE INVENTION

The present invention generally relates to needle assemblies used for injection of medication or withdrawal of blood or fluid samples. More specifically, the invention relates to an improvement in protecting a needle of the needle assembly when not in use to prevent unintentional contact with the needle.

Previously, injection needle assemblies have been used which employ a removable plastic cover. The cover fits over the needle portion and frictionally engages the assembly. After use, the cover may be replaced to guard the needle; however, such recapping is often dangerous and may result in unintentional contact with the point. Other prior art devices are known such as disclosed in U.S. Pat. Nos. 4,695,274, 4,801,295, 4,923,447, 4,929,232 and 4,929,237.

U.S. Pat. No. 4,695,274 discloses a safety needle attachment for a syringe body assembly using a needle holder with a needle fixed in the holder. The holder is constructed so as to apply and remove the syringe body assembly at will. The needle is initially surrounded by a protecting jacket releasably interlocked with the holder. When the needle is to be used, the interlock is released and the jacket telescopes over the holder to project the needle through a membrane over the end of the jacket to a working position. After use, the jacket is returned to its protecting position and interlocked in place.

U.S. Pat. No. 4,801,295 discloses a disposable combination of hypodermic syringe and needle having a sheath movable mounted on a syringe barrel to normally occupy a first position wherein the sheath extends to cover and protect the needle. In a second position of the sheath, the needle is at least partially exposed relative to the barrel and needle. In a third position of the sheath, the needle is covered by the sheath, and preferably, the sheath is irreversibly locked whereby abuse or misuse of this syringe and needle combination may be prevented.

U.S. Pat. No. 4,923,447 discloses a syringe assembly with an elongated tubular syringe barrel having a tubular needle mounted to one end and a plunger slidably disposed within the barrel. A hollow outer casing is mounted to one end and a plunger is slidably disposed within the barrel. A hollow outer casing is mounted to and surrounds the syringe barrel, and a tubular sleeve is telescopically disposed within the space between the casing and barrel and is movable between an extended position surrounding and shielding the syringe needle and a retracted position in which the needle is exposed for use. A longitudinal slot is formed in the casing and a projection mounted to the sleeve is slidably disposed within the slot to function as a lever for moving the sleeve between its extended and retracted position. Notches are formed on either end of the slots such that the projection may be moved laterally into a notch to lock the sleeve in either its extended or its retracted position.

U.S. Pat. No. 4,929,232 discloses a syringe having tamper evidence features including a barrel having a chamber for retaining fluid, an open proximal end, and a distal end having a passageway for fluid communication with the chamber. A needle shield having a longitudinal axis, a distal end and an open proximal end slidably engages the distal end of the barrel covering the passageway. The shield includes an outwardly projecting shield lug having a cam surface. A collar having an annular sidewall, an open proximal end and a distal end having an aperture therethrough is adjacent to the distal end of the barrel with the needle shield projecting distally through the aperture. The collar includes an inwardly projecting lug having a follower surface for contacting the cam surface. A lock is provided for releasably holding the collar adjacent to the barrel. The lock is positioned such that the force applied to the follower surface may disengage the lock allowing the collar to move and allowing the needle shield to be removed from the barrel.

U.S. Pat. No. 4,929,237 discloses a safety device for preventing contact with exposed contaminated hypodermic needles. A spring retracts the hypodermic needle, and safety elements prevent accidental removal of the syringe from a housing unit and exposure of the needle.

Such prior art devices are expensive both in terms of cost per assembly as well as in terms of costs associated with reusability. The prior art devices typically may only be capable of a single use and then disposed. Furthermore, the prior art devices typically may only receive a single size syringe into the needle assembly.

SUMMARY OF THE INVENTION

The present invention provides a sleeve for covering a needle. The sleeve includes a longitudinal groove and is slidably engaged to a hub within a needle assembly. The hub and the sleeve have a larger radius then the barrel of the syringe, and the needle is mounted within the hub. The sleeve is shifted to expose the needle by sliding it rearwardly over the hub with a spring compressing between the hub and the front end of the sleeve. After use, the sleeve cover may be moved back to recap the needle in its original protective position by the spring bias urging the sleeve cover forwardly while simultaneously urging the hub backwards.

In another embodiment, an I.V.-catheter assembly is provided with a sleeve cover slidably engaged to a hub within the I.V. assembly. The sleeve cover includes a longitudinal groove acting as a guide for a pin protruding radially from the hub. A spring in the I.V. assembly provides a self-recapping and locking feature between the sleeve cover and hub.

Additional features and advantages of the present invention are described in, and will be apparent from, the detailed description of the presently preferred embodiments and from the drawings.

BRIEF DESCRIPTION OF THE DRAWINGS

FIG. 1 is a perspective view of a needle assembly and cover of the prior art.

FIG. 2 is a perspective view of a second needle assembly and cover of the prior art.

FIG. 3 is a perspective view of a needle attachment for incorporation into a needle assembly in accordance with one aspect of the present invention.

FIG. 4 is a sectional view of the attachment of FIG. 3.

FIG. 5 is an illustration in cross section of the sliding cover recapping concept of one aspect of the present invention.

FIG. 6 illustrates one embodiment of the needle assembly of the prior art incorporating the sliding cover improvement of one aspect of the present invention.

FIG. 7 illustrates a second embodiment of the needle assembly of the prior art incorporating the sliding cover improvement of one aspect of the present invention.

FIG. 13 is a perspective view of a needle assembly in accordance with the present invention.

FIG. 14 is a partial cross-sectional view of a lock mechanism of the needle assembly of FIG. 13 in its unlocked position.

FIG. 15 is a cross-sectional view of the lock mechanism of the needle assembly of FIG. 13 in its locked position.

FIG. 16 is a cross-sectional view of the needle assembly of FIG. 13 in its engaged position.

FIG. 17 is a partial plan view of the groove in accordance with the present invention.

FIG. 18 is a cross-sectional view of the needle assembly of FIG. 13 in its recapped position.

DETAILED DESCRIPTION OF THE PRESENTLY PREFERRED EMBODIMENTS

Figure 8:
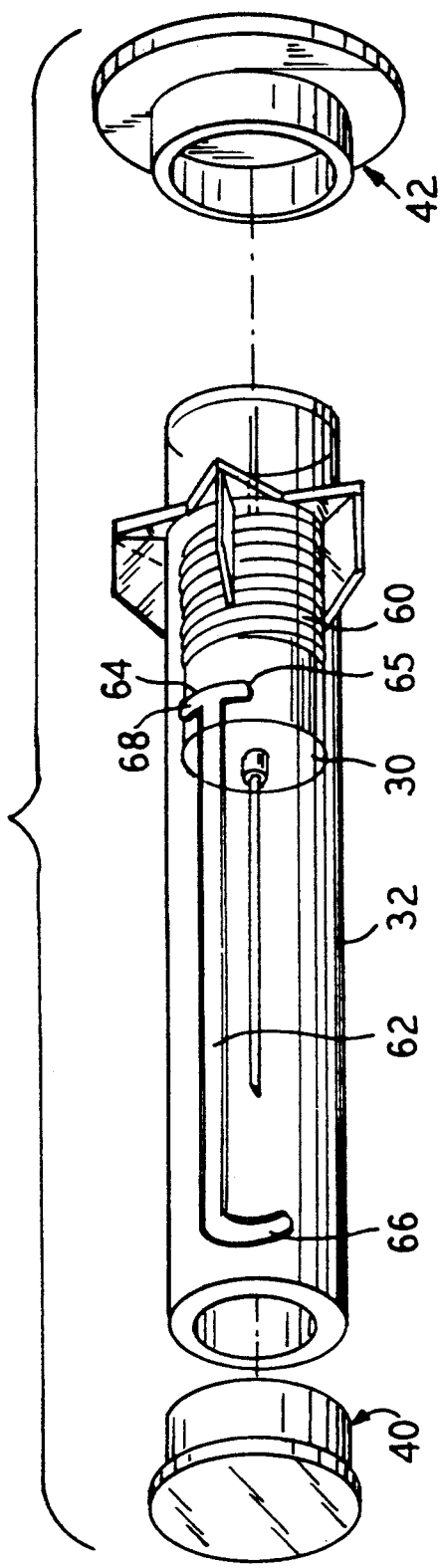
FIG. 8 is a perspective view of a needle assembly in accordance with a second aspect (self-recapping) of the present invention.
Figure 12:
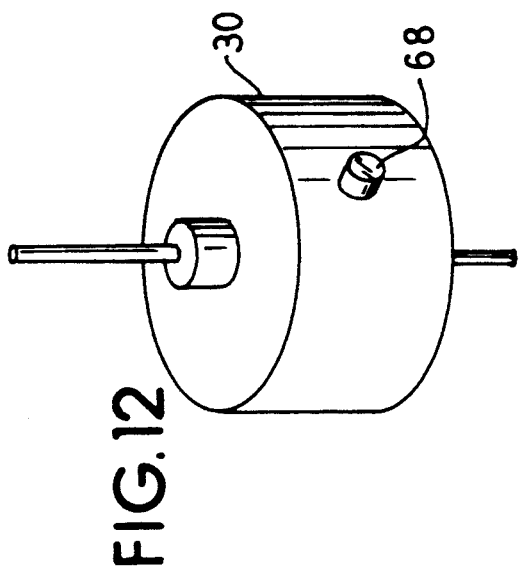
FIG. 12 is a perspective view of the hub of the assembly of FIG. 11.

Turning first to the prior art shown in FIGS. 1 and 2, there is depicted two versions of injection or hypodermic needle apparatus currently in use. In the first (FIG. 1) the apparatus consists of a syringe portion 10 having a barrel reservoir portion 12. A piston 14 reciprocates within the barrel to draw fluid into the reservoir or to eject fluid therefrom. In some instances the syringe is dispensed with the needle attached, as shown in FIG. 1. In a variation, the needle portion may be disposed separately; and the needle portion is attached to the syringe by friction or screw means. In either case, the cover 18 is provided as a cap over the needle and is removed prior to use. It may then be replaced after use in an attempt to protect against accidental contact with the needle. Unfortunately, this recapping all too frequently results in inadvertent contact with the needle.

A similar situation is presented with the injection needle apparatus depicted in FIG. 2. In this version the syringe barrel 20 is designed to accept an ampoule 22 and to eject the fluid therefrom. A separately dispensed needle assembly is attached by screw means to the barrel 20 and the needle extends into the ampoule 22. A needle cover 24 is removed to reveal the needle and, as before, the cover 24 is replaceable after use. In either instance, the sliding cover improvement described herein may be incorporated to initially reveal and to later recap the needle. Moreover, by use of the self-recapping technique described below, protection is greatly enhanced.

In an example of the sliding cover aspect of the present invention, there is shown in FIGS. 3-5 a needle attachment consisting of a hub 30 and a sliding sleeve cover 32. The needle is mounted within the hub (in accordance with prior art techniques) and projects a rear portion 34 to engage the reservoir 35 (or ampoule) of the syringe and a forward portion 36 to penetrate a patient's skin for injection. The radius of the hub 30, and therefore the inside diameter of the sleeve cover 32, are greater than that of the barrel reservoir 35, and this allows the barrel to telescope into the sleeve cover 32.

A cap 40 seals the forward portion of the sleeve and is removed prior to use. When the needle attachment is dispensed independent of the syringe, a rear cap 42 is provided to seal the rear portion of the sleeve. Removal of the rear cap 42 allows attachment of the needle to the syringe in accordance with well known friction or screw means. Typically, the hub 30 forms a receptacle to accept a fitting provided on the syringe barrel, and this receptacle operates to secure the hub 30 to the syringe.

When the needle assembly is attached, the rear portion 34 of the needle extends through the fitting to access the reservoir within the barrel of the syringe. Once the needle assembly is secured to the barrel, since the internal diameter of the sleeve cover is larger than the outside diameter of the barrel reservoir, the sleeve may now be shifted rearwardly (FIG. 5) to expose the forward portion of the needle. To facilitate this movement, the hub 30 and the internal surface of the sleeve cover 32 are smooth and form a sliding fit. An inwardly projecting annular lip 50 is provided on the forward end of the sleeve cover 32, and an annular lip 52 is provided on the rear extremity of the sleeve cover 32. These lips catch on the peripheral edge of the hub 30 when the sleeve cover 32 has been shifted fully to its forward or rearward position. After use, the sleeve may be easily shifted back to its original position, shielding the needle; and the forward cap 40 can then be safely replaced if desired. If the needle and cover assembly is removed from the barrel, the rear cap 42 can also be replaced.

Sliding movement of the cover is semi-automatic in a further feature of the invention. This accomplishes an instant self-recapping and is achieved by providing a spring bias in the form of a coil spring 60 (FIGS. 8-11) which acts to force the cover toward its protective position. The position of the cover is further controlled by a longitudinally aligned groove 62 having transverse legs 64, 65 and 66 defined at its extremities. A pin 68 protruding from the hub 30 travels within the groove 62; and when positioned within one of the transverse legs 64, 65 or 66, the pin 68 secures the cover against movement until manually unlocked.

To maintain the cover in its normal protective position, the coil spring 60 is fastened to the rear face of the hub 30 and a flange 70 at the rear of the cover. The unsprung condition of the spring 60 is the compressed state and it resists extension. Consequently, the spring 60 pulls the rear of the cover towards the hub 30 to maintain the cover 32 in the protective position. The cover is locked in this protective position by a slight rotation of the cover to position the pin 68 within transverse leg 64 of the groove 62. The ends of the assembly are sealed with forward and rear caps 40 and 42, as before, to protect the assembly during transport and handling.

To use the needle assembly, the end seals are removed, and the hub 30 is screwed onto the selected syringe. Due to the clockwise twist during syringe attachment, the pin 68 remains positioned in transverse leg 64. The professional may then counter rotate the cover 32 slightly to position the pin 68 in the longitudinal groove 62. In this position, the cover may then be shifted longitudinally to expose the needle, extending and tensioning the coil spring 60, and then twisted further counter clockwise to position the pin 68 within the arcuate extremity leg 66. Under tension from the spring 60, the pin 68 is held at the end of the arcuate leg 66 until released.

Figure 11:
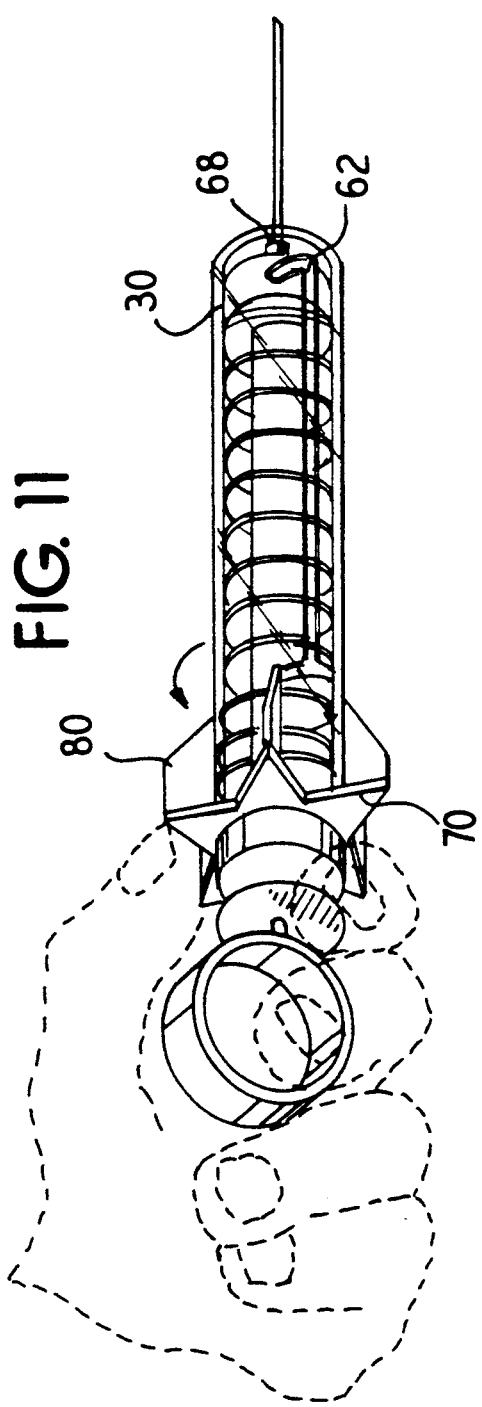
FIG. 11 is a perspective view of the self-recapping needle assembly illustrating the thumb release feature.
Figure 9:
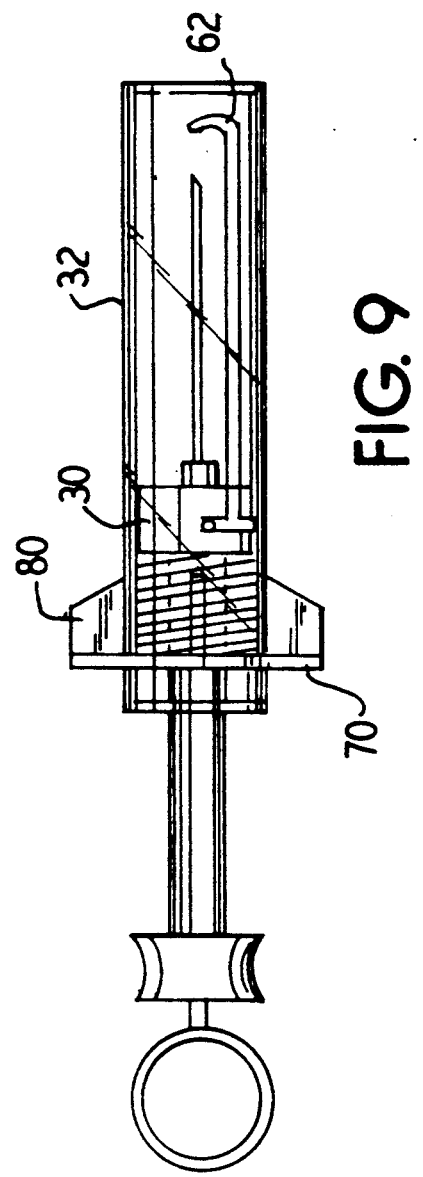
FIG. 9 is a sectional view of the needle assembly of FIG. 8 attached to a prior art syringe.
Figure 10:
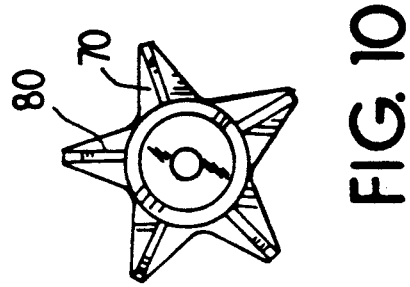
FIG. 10 is an end view of the needle assembly of FIG. 8.

As shown in FIG. 10, the rear portion of the cover exhibits fins 80 spaced around the cover and rigidly supported by a flange 70. Turning to FIG. 11, it can be seen that thumb pressure applied to one of the fins 80 causes the cover to rotate. This positions the pin 68 within the longitudinal groove 62, and automatically under spring tension, the cover 32 now snaps back to its protective position, safely recapping the needle. The needle assembly may now be safely resealed for disposal.

FIGS. 13-19 illustrate an improved embodiment of the sliding and self-recapping movements of the cover from that shown in FIGS. 8-12. A spring bias is provided in the form of a coil spring 60'. Unlike the embodiments shown in FIGS. 8-12, the spring 60' is secured within a circumferential longitudinal groove 72 of the hub 30. Furthermore, the spring 60' is front-loaded, that is, the spring 60' acts to force the cover 32 toward its protective position and is situated between the groove 72 in the hub 30' and the inwardly projecting annular lip 50 at the forward end of the sleeve cover 32.

To maintain the cover 32 in its normal protective position, the coil spring 60' is fastened between the longitudinal groove 72 within the hub 30' and the annular lip 50 at the front end of the cover 32. The spring 60', therefore, pushes the front of the cover 32 away from the hub 30' to maintain the cover 32 in the protective position.

The position of the cover 32 is further controlled by a longitudinally aligned groove 62' having a transverse arcuate leg 66' at one extremity and a triangular or pie-shaped opening 74 at its opposite extremity. The pin 68 protruding from the hub 30' travels within the groove 62 from transverse leg 66' through the groove 62' to the pie-shaped opening 74.

To use the needle assembly, the end seals (not shown) are removed, and the hub 30' is screwed onto the selected syringe 31 as illustrated in FIGS. 16 and 18. The pin 68 is positioned in the pie-shaped opening 74 and is allowed to travel in the longitudinal groove 62' by depressing a pie-shaped lock 76. The cover 32 may then be shifted longitudinally to expose the needle thereby compressing the coil spring 60'. The cover 32 may then be slightly rotated to lock the cover 32 into place by the pie-shaped lock 76 extending from the hub 30 at the end of the groove 62' in its transverse leg 66'.

Figure 19:
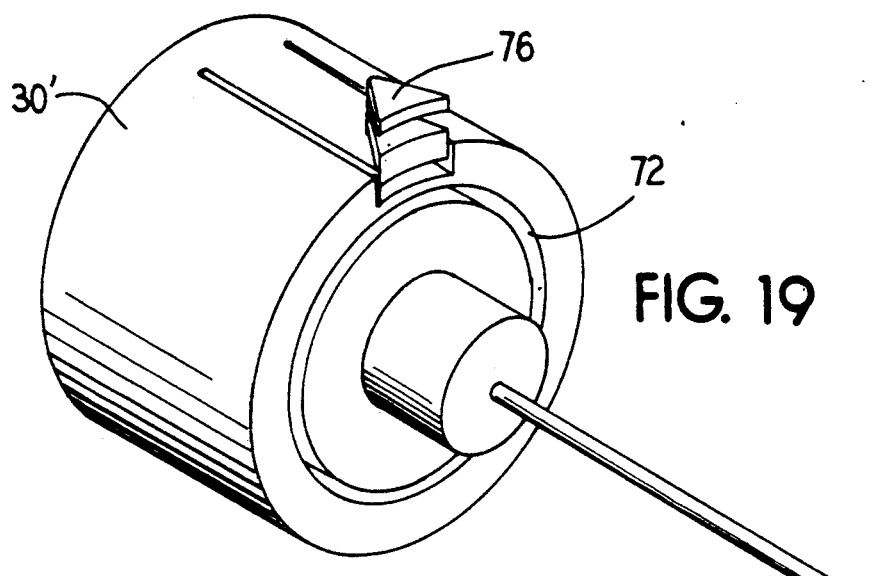
FIG. 19 is a perspective view of the hub of the assembly of FIG. 13.

The pie-shaped lock 76 as shown projecting from the hub 30' in FIG. 19 allows for clockwise or counter clockwise movement of the cover 32 when the cover 32 is being moved between its protected and non-protected positions. The front side of the lock 76 stops forward movement of the hub 30' but allows the lock 76 to move upward into a locked position after the end of the channel meets it. The arcuate transverse leg 66' simultaneously receives the pin 68 and secures the pin 68 in a fixed position at the extreme transverse point of the leg 66' from the groove 62'.

To implement the self-recapping aspect of the present invention, the pin 68 is forced from its position in the arcuate leg 66' by pressure and force applied to a fin 75 located around the periphery of the cover 32 and then travels along the groove 62'. Rotational movement of the cover 32 is predictable once forward and backward movement of the cover 32 is completed.

The pin 68 travels along the groove 62' and then enters the pie-shaped opening 74. With the spring 60' in its compressed state, the pin 68 will travel in the groove 62' and continue to the rearward most position of the pie-shaped opening 74. The walls of the pie-shaped opening 74 converge to a point at its most extreme end. If any rotational forces are present, the pin 68 reflects from the walls of the pie-shaped opening 74 and lodges itself at the point of the pie-shaped opening 74. In this position, the lock 76 is repositioned in its original, non-depressed state to prohibit any additional forward and backward motion of the cover 32 with respect to the hub 30'. The cover 32, therefore, under spring tension is forced to move by the spring 60' moving to its uncompressed state, and the cover 32 is now in its protective position in relation to the needle. The needle assembly may now be safely resealed for disposal.

FIGS. 20-23 illustrate an I.V. catheter assembly 100 implementing the sliding movement and self-recapping movement similar to that illustrated for the syringe assembly in FIGS. 13-19.

Figure 21:
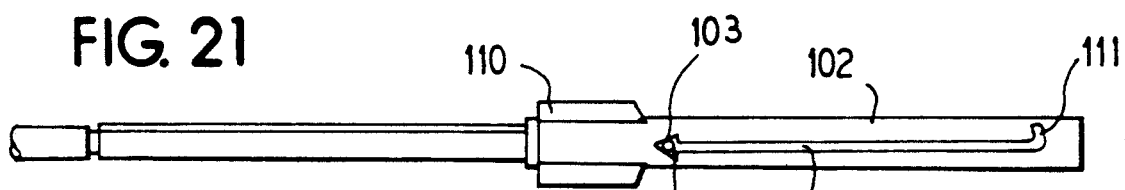
FIG. 21 is a plan view of the I.V. needle of FIG. 20 in its extended recapped position.
Figures 22, 23:
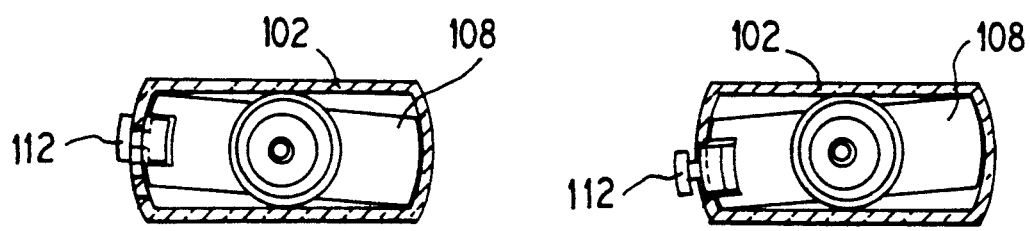
FIG. 22 is a cross-sectional view of the assembly of FIG. 20 in its locked and recapped position.
FIG. 23 is a cross-sectional view of the assembly of FIG. 20 in its unlocking position.

A sleeve 102 of the I.V. assembly 100 is substantially rectangular in cross-sectional shape as shown in FIGS. 22 and 23. The shorter opposite side walls are slightly arcuate with one of the two side walls including a longitudinal groove 104 in which a pin 106 protruding from a hub 108 of the assembly 100 travels within the sleeve 102 between locked and unlocked positions. A spring 109 is biased such that the sleeve 102 favors the covered or protective position as shown in FIG. 21.

The hub 108 is configured to permit partial rotation within the sleeve 102. Rotation of the hub 108 allows a locking mechanism 112 to be used with the self-recapping aspect of the assembly 100. The hub 108 and the sleeve 102 are designed to maintain a flat and narrow form to allow the needle to be placed as close and as parallel to the skin of a patient as possible.

To use the assembly 100, the hub 108 is forced to the forward end of the sleeve 102 against tension in the spring 109. The pin 106, therefore, travels along the longitudinal groove 104 until it reaches a transverse, arcuate leg 111. At this point, the sleeve 102 is slightly rotated to lock the hub 108 and needle projecting therefrom in an unprotective state.

Figure 20:
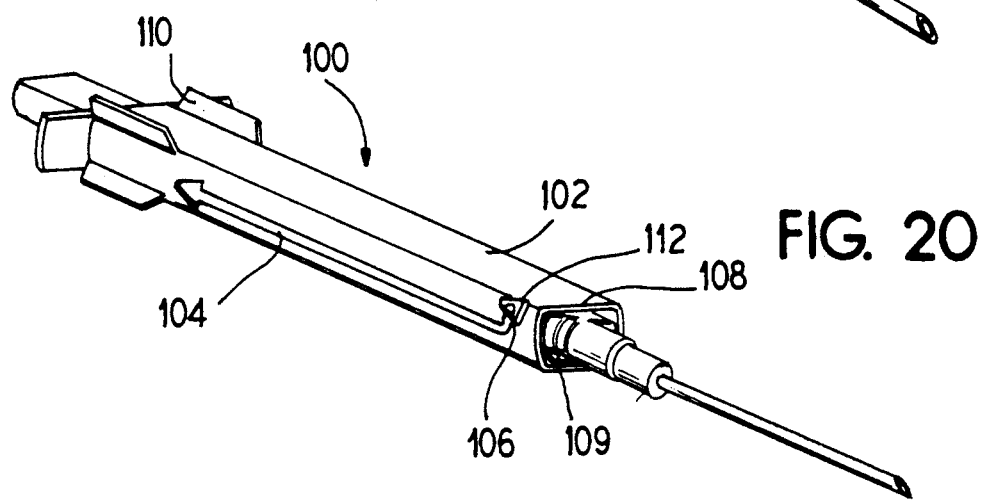
FIG. 20 is a perspective view of an I.V. needle implementing the self-recapping feature of the present invention.

When pressure is applied to the assembly 100 by, for example, exerting force upon a fin 110 protruding radially from the sleeve 102, the sleeve 102 partially rotates about the hub 108. With the sleeve 102 in its unprotected position as shown in FIG. 20, the spring 109 is in its compressed state. The pin 106 protruding from the hub 108 is, therefore, locked into the transverse, arcuate leg 111. To shift the sleeve 102 into its protected position, the pin 106 is forced into the longitudinal groove 104 from the arcuate leg 111. The pin 106 protruding from the hub 108 travels along the groove 104 to a pie-shaped opening 113 as previously described with reference to FIGS. 13-19.

The locking mechanism 112 protruding from the hub 108 as shown in FIGS. 22 and 23 locks the sleeve 102 into position by rotational movement of the hub 108 with respect to the sleeve 102 when the assembly 100 is in its unprotected position. The locking mechanism 112 prohibits further movement between the sleeve 102 and the hub 108.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim as my invention:

1. In an injection needle assembly having a barrel reservoir portion, a protruding needle affixed to the reservoir portion, and means for filling or emptying the reservoir portion through the needle comprising:

a hub defined about the needle proximate the conjunction of the needle with the reservoir portion, said hub having a circumferential groove;

a sleeve slidably engaged to said hub and selectively movable between a first position and a second position, said sleeve being arranged to extend over said needle when in said first position and to expose said needle and extend over said reservoir portion when in said second position;

means for urging said sleeve towards said first position, said means for urging between said circumferential groove at one end of said hub and at its opposite end by said sleeve;

means for releasably locking said sleeve in said second position; and means for releasing said sleeve from said second position to allow return of said sleeve to said first position.

2. The injection needle assembly of claim 1 wherein said means for releasably locking said sleeve comprises a longitudinal groove defined in said sleeve, and a pin positioned to protrude from said hub and to engage said groove, said groove further comprising a transverse leg at one end to secure said sleeve position relative to said hub in said first position.

3. The injection needle assembly of claim 2 wherein said longitudinal groove further comprises an opening at an opposite end from said transverse leg.

4. The injection needle assembly of claim 3 wherein said opening of said longitudinal groove is pie-shaped.

5. An improved needle attachment device for an injection needle assembly having a barrel reservoir portion adapted to receive the needle attachment and means for filling or emptying the reservoir portion through the needle, comprising:

a hub member having an outside diameter larger than the barrel portion and a circumferential groove having a diameter smaller than said outside diameter;

an injection needle mounted within said hub member;

a sleeve cover having an annular lip at its forward end, said sleeve cover slidably engaged to said hub and selectively movable between a first position and a second position, said sleeve cover being arranged to extend over the needle when in said first position and to expose the needle and extend over the barrel when in said second position;

means for urging said sleeve cover towards said first position, said means for urging between said circumferential groove of said hub member and at its opposite end by said annular lip of said sleeve cover;

means for releasably locking said sleeve cover in said second position; and means for releasing said sleeve cover from said second position to allow return to said first position.

6. The injection needle assembly of claim 5 wherein said means for releasably locking said sleeve cover comprises a longitudinal groove defined in said sleeve cover and a pin positioned to protrude from said hub and to engage said groove, said groove further comprising a transverse leg at one end to secure said sleeve cover position relative to said hub in said first position.

7. The injection needle assembly of claim 6 wherein said longitudinal groove further comprises an opening at an opposite end from said transverse leg.

8. The injection needle assembly of claim 7 wherein said opening is pie-shaped.

9. In an injection needle assembly having a barrel reservoir portion, a protruding needle affixed to the reservoir portion, and means for filling or emptying the reservoir portion through the needle comprising:

a hub defined about the needle proximate the conjunction of the needle with the reservoir portion, said hub having a circumferential groove;

a sleeve slidably engaged to said hub and selectively movable between a first position and a second position, said sleeve being arranged to extend over said needle when in said first position and to expose said needle and extend over said reservoir portion when in said second position;

means for urging said sleeve towards said first position, said means for urging between said circumferential groove at one end of said hub and at its opposite end by said sleeve;

means for releasably locking said sleeve in said second position;

means for releasing said sleeve from said second position to allow return of said sleeve to said first position;

wherein said means for releasably locking said sleeve comprises a longitudinal groove defined in said sleeve, and a pin positioned to protrude from said hub and to engage said groove, said groove further comprising a transverse leg at one end to secure said sleeve position relative to said hub in said second position; and wherein said means for releasing said sleeve comprises fins spaced about the outer periphery of the rear portion of said sleeve for causing selective rotation of said sleeve in response to pressure applied thereto.

10. The injection needle assembly of claim 9 further comprising front and rear cap means for closing the extremities of said sleeve.

11. In an injection needle assembly having a barrel reservoir portion, a protruding needle affixed to the reservoir portion, and means for filling or emptying the reservoir portion through the needle comprising:

a hub defined about the needle proximate the conjunction of the needle with the reservoir portion, said hub having a circumferential groove;

a sleeve slidably engaged to said hub and selectively movable between a first position and a second position, said sleeve being arranged to extend over said needle when in said first position and to expose said needle and extend over said reservoir portion when in said second position;

means for urging said sleeve towards said first position, said means for urging between said circumferential groove at one end of said hub and at its opposite end by said sleeve;

means for releasably locking said sleeve in said second position;

means for releasing said sleeve from said second position to allow return of said sleeve to said first position; and wherein said hub further comprises a locking means protruding from said hub to secure said sleeve relative to said hub.

12. An improved needle attachment device for an injection needle assembly having a barrel reservoir portion adapted to receive the needle attachment and means for filling or emptying the reservoir portion through the needle, comprising:

a hub member having an outside diameter equal to or larger than the barrel portion and a circumferential groove having a diameter smaller than said outside diameter;

an injection needle mounted within said hub member;

a sleeve cover having an annular lip at its forward end, said sleeve cover slidably engaged to said hub and selectively movable between a first position and a second position, said sleeve cover being arranged to extend over the needle when in said first position and to expose the needle and extend over the barrel when in said second position;

means for urging said sleeve cover towards said first position, said means for urging between said circumferential groove at one end of said hub member and at its opposite end by said annular lip of said sleeve cover;

means for releasably locking said sleeve cover in said second position;

means for releasing said sleeve cover from said second position to allow return to said first position; and wherein said means for releasing said sleeve cover comprises fins spaced about the outer periphery of the rear portion of said sleeve cover for causing selective rotation of said sleeve cover in response to pressure applied thereto.

13. The injection needle assembly of claim 12 further comprising front and rear cap means for closing the extremities of said sleeve cover.

14. An improved needle attachment device for an injection needle assembly having a barrel reservoir portion adapted to receive the needle attachment and means for filling or emptying the reservoir portion through the needle, comprising:

a hub member having an outside diameter equal to or larger than the barrel portion and a circumferential groove having a diameter smaller than said outside diameter;

an injection needle mounted within said hub member;

a sleeve cover having an annular lip at its forward end, said sleeve cover slidably engaged to said hub and selectively movable between a first position and a second position, said sleeve cover being arranged to extend over the needle when in said first position and to expose the needle and extend over the barrel when in said second position;

means for urging said sleeve cover towards said first position, said means for urging between said circumferential groove at one end of said hub member and at its opposite end by said annular lip of said sleeve cover;

means for releasably locking said sleeve cover in said second position;

means for releasing said sleeve cover from said second position to allow return to said first position; and wherein said hub member further comprises a locking means protruding from said hub member to secure said sleeve cover relative to said hub member.

15. The injection needle assembly of claim 11 wherein said locking means is pie-shaped.

16. The injection needle assembly of claim 14 wherein said locking means is pie-shaped.

* * * * *